United States Patent
Rimoldi et al.

(10) Patent No.: US 6,497,879 B1
(45) Date of Patent: *Dec. 24, 2002

(54) IMMUNOGENIC COMPOSITIONS OF TUMOR REJECTION ANTIGEN PRECURSOR MAGE-10 AND AN ADJUVANT

(75) Inventors: Donata Rimoldi, Epalinges (CH); Victor Jongeneel, Epalinges (CH); Pierre Coulie, Brussels (BE); Jean-Charles Cerrottini, Epalinges (CH); Stefan Carrel, Epalinges (CH); Daryl Reed, Epalinges (CH)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/589,717

(22) Filed: Jun. 8, 2000

Related U.S. Application Data

(60) Continuation of application No. 09/089,595, filed on Jun. 2, 1998, now Pat. No. 6,153,728, which is a division of application No. 08/724,774, filed on Oct. 3, 1996, now Pat. No. 5,908,778.

(51) Int. Cl.[7] .................................................. A61K 39/42
(52) U.S. Cl. ................................. 424/184.1; 424/185.1; 424/277.1
(58) Field of Search ................................. 530/300, 324; 536/23.1; 424/184.1, 185.1, 277.1

(56) References Cited

U.S. PATENT DOCUMENTS 6,153,728 A * 11/2000 Rimoldi et al. ............. 530/300

OTHER PUBLICATIONS

DePlaen et al, Immunogenetics vol. 40 p. 360 (1994).*
Campbell, Monoclonal Antibody Technology ed. Elsevier Science Publisher p. 1–29 (1986).*
Database Genbank, Accession No. U10685, Jun. 1995.*

* cited by examiner

*Primary Examiner*—Sheela Huff
(74) *Attorney, Agent, or Firm*—Fulbright & Jaworski L.L.P.

(57) ABSTRACT

Isolated cDNA molecules which encode the tumor rejection antigen precursor MAGE-10, the protein itself, antibodies to it, and uses of these are a part of the invention.

3 Claims, 2 Drawing Sheets

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 19 nucleotides
      (B) TYPE: nucleic acid
      (C) STRANDEDNESS: single
      (D) TOPOLOGY: linear (xi) SEQUENCE DESCRIPTION: SEQ ID NO: 1:

GTGGCGACGA    CTCCTGGAG                              19

(2) INFORMATION FOR SEQ ID NO: 2:

(i) SEQUENCE CHARACTERISTICS:
      (A) LENGTH: 23 nucleotides
      (B) TYPE: nucleic acid
      (C) STRANDEDNESS: single
      (D) TOPOLOGY: linear (xi) SEQUENCE DESCRIPTION: SEQ ID NO: 2:

CAGACCAACT  GGTAATGATA  GCG                        23

(2) INFORMATION FOR SEQ ID NO: 3:

(i) SEQUENCE CHARACTERISTICS:
      (A) LENGTH: 2559 nucleotides
      (B) TYPE: nucleic acid
      (C) STRANDEDNESS: single
      (D) TOPOLOGY: linear (xi) SEQUENCE DESCRIPTION: SEQ ID NO: 3:

| | | | | |
|---|---|---|---|---|
| TCCGGGGTCG | CTCGAGCCGG | CCGGGACTCG | GGGATCASAA | GTAACGGCGG | 50 |
| YYMKYGTKCT | GAGGGACAGG | CTTGAGATCG | GCTGAAGAGA | GCGGGCCCAG | 100 |
| GCTCTGTGAG | GAGGCAAGGG | AGGTGAGAAC | CTTGCTCTCA | GAGGGTGACT | 150 |
| CAAGTCAACA | CAGGGAACCC | CTCTTTTCTA | CAGACACAGT | GGGTCGCAGG | 200 |
| ATCTGACAAG | AGTCCAGGTT | CTCAGGGGAC | AGGGAGAGCA | AGAGGTCAAG | 250 |
| AGCTGTGGGA | CACCACAGAG | CAGCACTGAA | GGAGAAGACC | TGCCTGTGGG | 300 |
| TCCCCATCGC | CCAAGTCCTG | CCCACACTCC | CACCTGCTAC | CCTGATCAGA | 350 |
| GTCATCATGC | CTCGAGCTCC | AAAGCGTCAG | CGCTGCATGC | CTGAAGAAGA | 400 |
| TCTTCAATCC | CAAAGTGAGA | CACAGGGCCT | CGAGGGTGCA | CAGGCTCCCC | 450 |
| TGGCTGTGGA | GGAGGATGCT | TCATCATCCA | CTTCCACCAG | CTCCTCTTTT | 500 |
| CCATCCTCTT | TTCCCTCCTC | CTCCTCTTCC | TCCTCCTCCT | CCTGCTATCC | 550 |
| TCTAATACCA | AGCACCCCAG | AGGAGGTTTC | TGCTGATGAT | GAGACACCAA | 600 |
| ATCCTCCCCA | GAGTGCTCAG | ATAGCCTGCT | CCTCCCCCTC | GGTCGTTGCT | 650 |
| TCCCTTCCAT | TAGATCAATC | TGATGAGGGC | TCCAGCAGCC | AAAAGGAGGA | 700 |
| GAGTCCAAGC | ACCCTACAGG | TCCTGCCAGA | CAGTGAGTCT | TTACCCAGAA | 750 |
| GTGAGATAGA | TGAAAAGGTG | ACTGATTTGG | TGCAGTTTCT | GCTCTTCAAG | 800 |
| TATCAAATGA | AGGAGCCGAT | CACAAAGGCA | GAAATACTGG | AGAGTGTCAT | 850 |
| AAAAAATTAT | GAAGACCACT | TCCCTTTGTT | GTTTAGTGAA | GCCTCCGAGT | 900 |
| GCATGCTGCT | GGTCTTTGGC | ATTGATGTAA | AGGAAGTGGA | TCCCACTGGC | 950 |
| CACTCCTTTG | TCCTTGTCAC | CTCCCTGGGC | CTCACCTATG | ATGGGATGCT | 1000 |
| GAGTGATGTC | CAGAGCATGC | CCAAGACTGG | CATTCTCATA | CTTATCCTAA | 1050 |
| GCATAATCTT | CATAGAGGGC | TACTGCACCC | CTGAGGAGGT | CATCTGGGAA | 1100 |
| GCACTGAATA | TGATGGGGCT | GTATGATGGG | ATGGAGCACC | TCATTTATGG | 1150 |
| GGAGCCCAGG | AAGCTGCTCA | CCCAAGATTG | GGTGCAGGAA | AACTACCTGG | 1200 |
| AGTACCGGCA | GGTGCCTGGC | AGTGATCCTG | CACGGTATGA | GTTTCTGTGG | 1250 |
| GGTCCAAGGG | CTCATGCTGA | AATTAGGAAG | ATGAGTCTCC | TGAAATTTTT | 1300 |
| GGCCAAGGTA | AATGGGAGTG | ATCCAAGATC | CTTCCCACTG | TGGTATGAGG | 1350 |
| AGGCTTTGAA | AGATGAGGAA | GAGAGAGCCC | AGGACAGAAT | TGCCACCACA | 1400 |
| GATGATACTA | CTGCCATGGC | CAGTGCAAGT | TCTAGCGCTA | CAGGTAGCTT | 1450 |
| CTCCTACCCT | GAATAAAGTA | AGACAGATTC | TTCACTGTGT | TTTAAAAGGC | 1500 |
| AAGTCAAATA | CCACATGATT | TTACTCATAT | GTGGAATCTA | AAAAAAAAAA | 1550 |
| AAAAAAAGT | TGGTATCATG | GAAGTAGAGA | GTAGAGCAGT | AGTTACATTA | 1600 |
| CAATTAAATA | GGAGGAATAA | GTTCTAGTGT | TCTATTGCAC | AGTAGGATGA | 1650 |
| CTATAGTTAA | CATTAAGATA | TTGTATATTA | CAAAACAGCT | AGAAGGAAGG | 1700 |
| CTTTTCAATA | TTGTCACCAA | AAAGAAATGA | TAAATGCATG | AGGTGATGGA | 1750 |
| TACACTACCT | GATGTGATCA | TTATACTACA | TATACATGAA | TCAGAACATC | 1800 |
| AAATTGTACC | TCATAAATAT | CTACAATTAC | ATGTCAGTTT | TGTTTATGT | 1850 |
| TTTTGTTTTT | TTTAATTTA | TGAAAACAAA | TGAGAATGGA | AATCAATGAT | 1900 |
| GTATGTGGTG | GAGGGCCAGG | CTGAGGCTGA | GGAAAATACA | GTGCATAACA | 1950 |

-continued

```
TCTTTGTCTT ACTGTTTTCT TTGGATAACC TGGGGACTTC TTTTCTTTTC        2000

TTCTTGGTAT TTTATTTTCT TTTTCTTCTT CTTCTTTTTT TTTTTTAACA        2050

AAGTCTCACT CTATTGCTCT GGCAGGAGTG CAGTGGTGCA GTCTCGGCTC        2100

ACTGCAACTT CCGCCTCCTG GGTTCAAGCG ATTCTCCTGC CTCAGTCTCC        2150

TGAGTAGCTG GGATTACAAG TGTGCACCAC CATACCCGGC TAATTTTGTA        2200

TTTTTTAGTA GAGATGGGGT TTCACCATGT TGGCCAGGCT GGTCTCAAAC        2250

TCCTGACCTC AGGTAATCTG CCCGCCTCAG CCTCCCAAAG TGCTGGGATA        2300

ACAGGTGTGA GCCCACTGCA CCCCAGCCTC TTCTTGGTAT TTTAAAATGT        2350

TGTTACTTTT ACTAGAATGT TTATGAGCTT CAGAATCTAA GGTCACACGT        2400

TCGTTTCTGT TTATCCAGTT TAAGAAACAG TTTTGCTATT TTGTAAAACA        2450

AATTGGGAAC CCTTCCATCA TATTTGTAAT CTTTAATAAA ATAACATGGA        2500

ATTGGAATAG TAATTTTCTT GGAAATATGA AAAAATAGTA AAATAGAGAA        2550

AATAATTTT                                                     2559
```

(2) INFORMATION FOR SEQ ID NO: 4:

(i) SEQUENCE CHARACTERISTICS:
        (A) LENGTH: 28
        (B) TYPE: amino acid
        (D) TOPOLOGY: linear (xi) SEQUENCE DESCRIPTION: SEQ ID NO: 4:

```
Gln Asp Arg Ile Ala Thr Thr Asp Asp Thr Thr Ala Met Ala Ser Ala
                 5                  10                  15
Ser Ser Ser Ala Thr Gly Ser Phe Ser Tyr Pro Glu
            20                  25
```

(2) INFORMATION FOR SEQ ID NO: 5:

(i) SEQUENCE CHARACTERISTICS:
        (A) LENGTH: 21
        (B) TYPE: amino acid
        (D) TOPOLOGY: linear (xi) SEQUENCE DESCRIPTION: SEQ ID NO: 5:

```
Phe Asn Asn Phe Thr Val Ser Phe Trp Leu Arg Val Pro Lys Val Ser
                 5                  10                  15
Ala Ser His Leu Glu
            20
```

IMMUNOGENIC COMPOSITIONS OF TUMOR REJECTION ANTIGEN PRECURSOR MAGE-10 AND AN ADJUVANT

RELATED APPLICATIONS

This application is a continuation of application Ser. No. 09/089,595, filed Jun. 2, 1998, now U.S. Pat. No. 6,153,728, which is a divisional of application Ser. No. 08/724,774, filed on Oct. 3, 1996, now U.S. Pat. No. 5,908,778.

FIELD OF THE INVENTION

This invention relates to tumor rejection antigen precursors, the nucleic acid molecules encoding them, antibodies specific to these, and uses thereof.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18: 769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53: 333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum$^-$ antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, tum$^-$ antigens are obtained by mutating tumor cells which do not generate an immune response in syngeneic mice and will form tumors (i.e., "tum$^+$" cells). When these tum$^+$ cells are mutagenized, they are rejected by syngeneic mice, and fail to form tumors (thus "tum$^-$"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43: 125 (1983).

It appears that tum variants fail to form progressive tumors because they initiate an immune rejection process. The evidence in favor of this hypothesis includes the ability of "tum$^-$" variants of tumors, i.e., those which do not normally form tumors, to do so in mice with immune systems suppressed by sublethal irradiation, Van Pel et al., Proc. Natl. Acad. Sci. USA 76: 5282–5285 (1979); and the observation that intraperitoneally injected tum cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same tum variant, even when immunosuppressive amounts of radiation are administered with the following challenge of cells (Boon et al., Proc. Natl, Acad. Sci. USA 74: 272–275 (1977); Van Pel et al., supra; Uyttenhove et al., supra). Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearon et al., Cancer Res. 48: 2975–1980 (1988) in this regard.

A class of antigens has been recognized which are presented on the surface of tumor cells and are recognized by cytolytic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells presenting the tumor rejection antigens are lysed. Characterization studies have identified CTL clones which specifically lyse cells expressing the tumor rejection antigens. Examples of this work may be found in Levy et- al., Adv. Cancer Res. 24: 1–59 (1977); Boon et al., J. Exp. Med. 152: 1184–1193 (1980); Brunner et al., J. Immunol. 124: 1627–1634 (1980); Maryanski et al., Eur. J. Immunol. 124: 1627–1634 (1980); Maryanski et al., Eur. J. Immunol. 12: 406–412 (1982); Palladino et al., Canc. Res. 47: 5074–5079 (1987). This type of analysis is required for other types of antigens recognized by CTLs, including minor histocompatibility antigens, the male specific H-Y antigens, and the class of antigens referred to as "tum$^-$" antigens, and discussed herein.

A tumor exemplary of the subject matter described supra is known as P815. See DePlaen et al., Proc. Natl. Acad. Sci. USA 85: 2274–2278 (1988); Szikora et al., EMBO J 9: 1041–1050 (1990), and Sibille et al., J. Exp. Med. 172: 35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum variants following mutagenesis, including variants referred to as P91A (DePlaen, supra), 35B (Szikora, supra), and P198 (Sibille, supra). In contrast to tumor rejection antigens—and this is a key distinction—the tum$^-$ antigens are only present after the tumor cells are mutagenized. Tumor rejection antigens are present on cells of a given tumor without mutagenesis. Hence, with reference to the literature, a cell line can be tum$^+$, such as the line referred to as "P1", and can be provoked to produce tum⁻ variants. Since the tum⁻ phenotype differs from that of the parent cell line, one expects a difference in the DNA of tum cell lines as compared to their tum⁺ parental lines, and this difference can be exploited to locate the gene of interest in tum⁻ cells. As a result, it was found that genes of tum⁻ variants such as P91A, 35B and P198 differ from their normal alleles by point mutations in the coding regions of the gene. See Szikora and Sibille, supra, and Lurquin et al., Cell 58: 293–303 (1989). This has proved not to be the case with the TRAs of this invention. These papers also demonstrated that peptides derived from the tum⁻ antigen are presented by the $L^d$ molecule for recognition by CTLs. P91A is presented by $L^d$, P35 by $D^d$ and P198 by $K^d$.

PCT application PCT/US92/04354, filed on May 22, 1992 assigned to the same assignee as the subject application, teaches a family of human tumor rejection antigen precursor coding genes, referred to as the MAGE family. Several of these genes are also discussed in van der Bruggen et al., Science 254: 1643 (1991). It is now clear that the various genes of the MAGE family are expressed in tumor cells, and can serve as markers for the diagnosis of such tumors, as well as for other purposes discussed therein. See also Traversari et al., Immunogenetics 35: 145 (1992); van der Bruggen et al., Science 254: 1643 (1991) and De Plaen, et al., Immunogenetics 40: 360 (1994).

U.S. Pat. No. 5,342,774, cited supra and incorporated by reference, teaches various members of the MAGE family of TRAPS, in genomic DNA and cDNA form. Genomic DNA for MAGE-10 is taught in PCT application PCT/US92/04354, cited supra, in SEQ ID NO: 22, as a 920 base pair fragment. DePlaen, et al., Immunogenetics 40: 360–369 (1994), discusses PCR work which identified a 485 nucleotide portion of MAGE-10. Also, see Genbank Accession No. U10685, incorporated by reference. A cDNA molecule, however, is not discussed.

The previously cited PCT application discusses antibodies to MAGE proteins generally. Chen et al., U.S. Pat. No. 5,541,104, to Chen et al., incorporated by reference, teaches monoclonal antibodies which specifically bind to tumor rejection antigen precursor MAGE-1. This patent is incorporated by reference. In order to prepare the monoclonal antibodies, Chen et al produced a MAGE-1 TRAP in *E. coli* which was not full length, because of difficulties with expression of the full length molecule.

It has now been found, however, that monoclonal antibodies which bind to both MAGE-1 and MAGE-10 TRAP can be produced. This is surprising in view of the reports in the literature, because it was not seen to be possible to produce such antibodies with the available information on MAGE-10. The TRAP encoded by the cDNA for MAGE-10 is found to be a molecule of about 72 kilodaltons molecular weight, on SDS-PAGE. It has also been found that polyclonal antibodies specific to MAGE-10 can be produced. These, as well as other aspects of the invention, are set forth in the disclosure which follows.

DETAILED DESCRIPTION OF PREFERRED EMBODIMENTS

EXAMPLE 1

Figure 1:
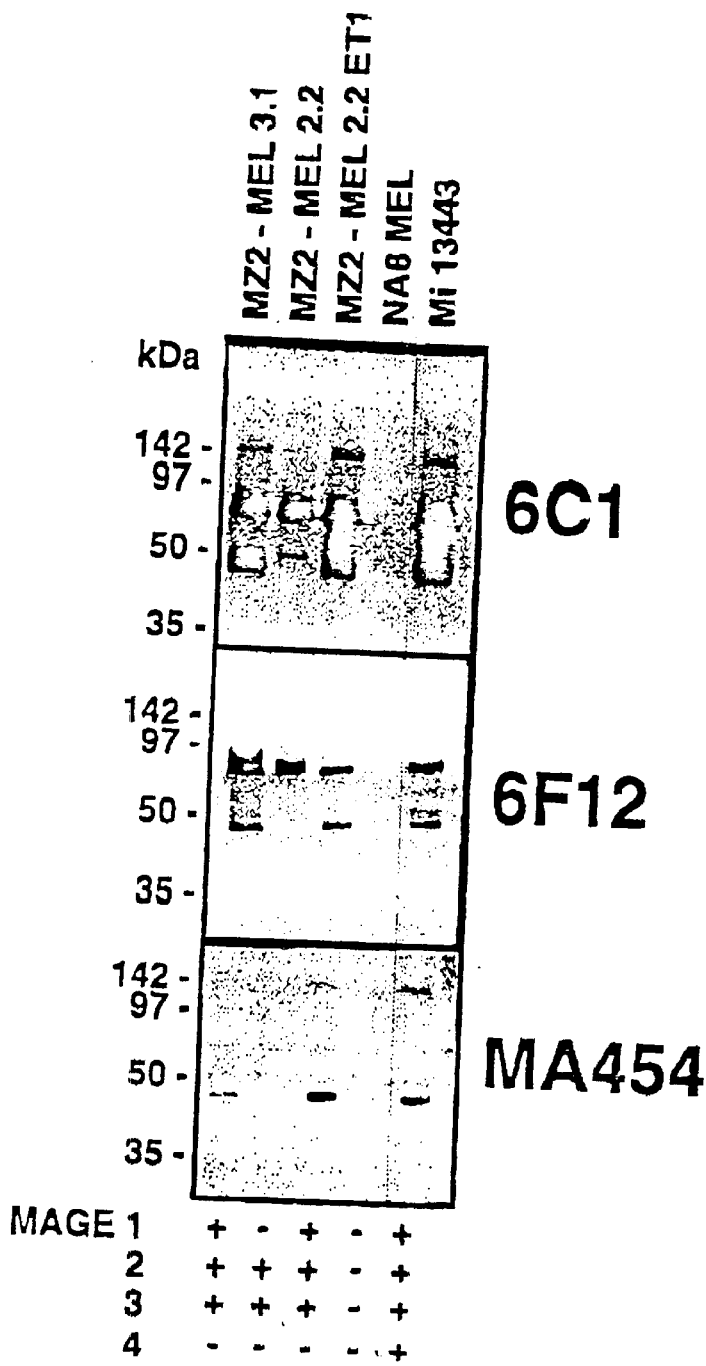
FIG. 1 presents results of a Western blotting assay, using electrochemiluminescence detection to test reactivity of monoclonal antibodies with various cell lysates.

Full length recombinant MAGE-1 protein was prepared in the form of a fusion protein, in *E. coli*. See Schultz-Thater, et al., Int. J. Cancer 59: 435–439 (1994), incorporated by reference. Briefly, full length MAGE-1 cDNA was cloned into a well known expression vector, pET 16b. This vector permits expression of a fusion protein which contains 10 histidine molecules at the N-terminus. The *E. coli* were cultured, following Schultz-Thater, after which the cells were lysed, and the recombinant fusion protein was purified on a $Ni^{2+}$ column. The purified material, when tested by SDS-PAGE, showed a major band of 48 kilodaltons. This 48 kD material was used in the experiments which follow.

EXAMPLE 2

Following the production of the recombinant MAGE-1 fusion protein, a BALB/c mouse was immunized intraperitoneally, twice, with 20 ug of the recombinant protein each time, in a composition which contained complete Freund's adjuvant. This was followed by two additional injections, each of 20 ug of recombinant MAGE-1, with incomplete Freund's adjuvant. The spleen cells of the mouse were then fused with NS-1 myeloma cells, in accordance with Carrel, et al., Cancer Res. 40: 2523–2528 (1980). The resulting hybridoma cells were cultured, and supernatants from the cultures were screened, using an ELISA, to determine if recombinant MAGE-1 specific monoclonal antibodies were being produced. The ELISA involved coating recombinant MAGE-1 protein (250 ng/50 ul per well), followed by overnight incubation at 4° C. Samples of supernatant were added, followed by biotin conjugated sheep antimouse Ig, and streptavidin-alkaline phosphatase conjugate.

The ELISA resulted in the identification of 289 hybridomas which produced antibodies against recombinant MAGE-1.

EXAMPLE 3

In the next set of experiments, the antibodies were tested to determine if they could be used to immunostain cells which were positive for mRNA for MAGE-1.

Initially the hybridomas were screened to try to eliminate any cross reactive monoclonals. To do this, cell lines with known, and different patters of MAGE-TRAP expression were tested. MZ2-MEL 3.1 is known to express all of MAGE-1, 2, 3 and 4; MZ2-MEL 2.2 expresses MAGE-2 and 3; and U251, a glioblastoma cell line negative for all four, were tested. Cells were cultured in 16 well plastic chambers, fixed in cold acetone (0° C. for five minutes), and then stored until ready to use at −20° C. Endogenous peroxidase was then blocked with 0.3% $H_2O_2$ (10 minutes), and the cells were then preincubated, in 0.1% bovine serum albumin in phosphate buffered saline, for 30 minutes. This produced a first layer of a three layer biotin/avidin/peroxidase system as described by Carrel, et al., supra. Following the fixing of the cells, goat anti-mouse IgG biotin conjugate was added (following 1:50 dilution), to yield the second layer. Finally, avidin-peroxidase conjugates were added, following dilution at 1:1000. In the case of the second and third layers, incubation was for 30. minutes and then 15 minutes. Peroxidase was visualized with amino-ethylcarbazole, and counter staining of cells, using Gill's hematoxylin for 30 seconds. This set of experiments results in the discovery that two mAbs, i.e., 6C1 and 6F2, stained only the MZ2-MEL 3.1 cells. These two clones were then used in a series of experiments on cells which had been tested for mRNA for MAGE-1, 2, 3 and 4. Cells were classified as being positive or negative for MAGE-1 mRNA expression. This was determined by following the procedures of Rimoldi et al., Int. J. Cancer 54: 527–528 (1993); Brasseur et al., Int. J. Cancer 63: 375–380 (1995). In brief, total RNA was extracted from cell samples using well known, commercially available methods and reagents, and then subjected to reverse transcription and polymerase chain reaction using MAGE-1, MAGE-2, MAGE-3 and MAGE-4 specific primers. See Brasseur, et al. supra. Table 1, which follows, presents the results of this work. It shows that, regardless of status of MAGE-2, 3 or 4 expression both mAbs stained all MAGE-1 positive cells.

TABLE I

IMMUNOCYTOCHEMICAL REACTIVITY OF MAbs 6Cl AND 6F12 WITH VARIOUS CELL LINES

| Cell lines | Immunostaining[1] | | MAGE-mRNA expression[2] |
|---|---|---|---|
| | MAb 6Cl | MAb 6F12 | |
| [a]MZ2-MEL 3.1 | + | + | $1^\oplus, 2^\oplus, 3^\oplus, 4^\oplus$ |
| [a]MZ2-MEL 2.2 | − | − | $1^-, 2^\oplus, 3^\oplus, 4^-$ |
| [a]MZ2-MEL 2.2 ET1 | + | + | $1^\oplus, 2^\oplus, 3^\oplus, 4^-$ |
| [b]Me235 | + | + | $1^\oplus, 2^\oplus, 3^\oplus, 4^-$ |
| [b]Mi13443 | + | + | $1^\oplus, 2^\oplus, 3^\oplus, 4^\oplus$ |
| [b]NA8-MEL | − | − | $1^-, 2^-, 3^-, 4^-$ |
| [b]Me220 | − | − | $1^-, 2^-, 3^-, 4^-$ |
| [a]Me241-2 | + | + | $1^\oplus, 2^-, 3^-, 4^-$ |
| [a]Mi9 | − | − | $1^-, 2^\oplus, 3^\oplus, 4^-$ |
| [a]Mi13 | − | − | $1^-, 2^\oplus, 3^\oplus, 4^-$ |
| [a]Mi21 | − | − | $1^-, 2^-, 3^\oplus, 4^-$ |
| [b]U251 | − | − | $1^-, 2^-, 3^-, 4^-$ |
| [c]MCF7 | − | − | $1^-, 2^-, 3^-, 4^-$ |
| [d]FeK4 | − | − | $1^-, 2^-, 3, 4^-$ |
| [e]P815 | − | − | $1^-, 2^-, 3^-, 4^-$ |
| [f]P815/MAGE-1 | + | + | $1^\oplus, 2^-, 3, 4^-$ |
| [g]HEL | + | + | $1^\oplus, 2^-, 3^-, 4^-$ |
| [g]TF1 | − | − | $1^-, 2^-, 3^\oplus, 4^-$ |

[a]Melanoma; [b]glioblastoma; [c]breast carcinoma; [d]fibroblast; [e]mouse mastocytoma; [f]mouse mastocytoma transfected with MAGE-1 cDNA; [g]myeloid luekemia.
[1]Acetone-fixed cells were stained by a 3-layer biotin/avidin/peroxidase system.
[2]The cellular mRNA was reverse transcribed and the cDNA tested by PCR using primers specific for MAGE-1, -2, -3 or -4 sequences.

EXAMPLE 4

A further set of experiments were then carried out, using the well known Western blotting technique. Five cell lines were tested, i.e., MZ2-MEL 3.1, MZ2-MEL 2.2, MZ2-MEL 2.2 ET1, NA8 MEL, and Mi13443. All of these lines are presented in Table 1, supra. Cells were cultured, and then lysed in a Nonidet P40 (NP-40) buffer (150 mM NaCl, 0.5k NP-40, 2 mM EDTA, 80 mM Tris-HCl, pH 7.5, 0.02% NaN$_3$, 100 ug/ml PMSF and 100 ug/ml aprotinin). Approximately 50 ug aliquots were then subjected to SDS-PAGE under reducing conditions, and the thus separated proteins were transferred to nitrocellulose paper. Undiluted hybridoma supernatants, and a standard, commercially available electrochemiluminescence detection system was used. FIG. I shows these results. The were intriguing because two major bands were found by both mAbs when testing MZ2-MEL 3.1. These bands are at 46 and 72 kilodaltons. The known MAGE-1 specific monoclonal antibody MA454 (Chen, et al., Proc. Natl. Acad. Sci. USA 91: 1004–1008 (1994); U.S. Pat. No. 5,541,104)) did not detect anything in MAGE-1 negative cell line MZ2-MEL 2.2, but when this cell line was transfected with MAGE-1 cDNA (to become cell line MZ2-MEL 2.2 ET1), MA 454 mAb did bind to a 46 kD band. one concludes from this that the 46 kilodalton species bound by all of MA454, 6C1, and 6F12 is MAGE-1 protein, but that the latter two mAbs are cross reactive with a second, 72 kilodaltons protein which was expressed by MZ2-MEL 3.1, MZ2-MEL 25 2.2, and Mi13443 (as well as transfected MZ2 MEL 2.2. ET1). Note, however, that MZ2-MEL 2.2 is MAGE-1 negative, suggesting that the cross reactivity is with a non-MAGE-1 protein.

EXAMPLE 5

Figure 2:
FIG. 2 presents results of tests designed to determine if cell line NA8-MEL could be induced to produce 72 kilodalton protein in the presence of MAGE-1 cDNA.
Figure 2:
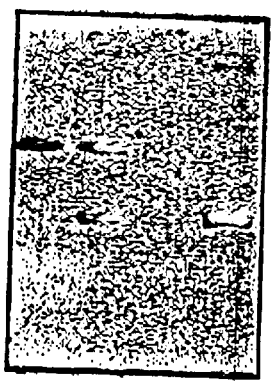

The fact that NA8-MEL did not express any of MAGE-1, 2, 3 or 4 and did not produce any proteins which bound to any of the three mAbs tested, made it useful in experiments to determine whether or not detection of the 72 kDa protein was dependent on presence of MAGE-1. The NA8-MEL cells were transiently transfected with MAGE-1 cDNA in plasmid pcDNAI, using lipofectin. The transfected cells were lysed, and analyzed via Western blotting, as described supra, using 6C1 and 6F12. A band of 46 kilodaltons resulted, as did a faint band corresponding to what is believed to be a multimeric form of MAGE-1. See FIG. 2. No 72 kDa band was found, however. There was no 72 kDa protein found following transient transfection with each of MAGE-2, 3, 4 and 12. This was also true with COS-7 cells, following transient transfection.

EXAMPLE 6

In view of the unexpected presence of the 72 kDalton band, Western blotting was carried out in accordance with the procedures set forth supra, on a large number of cells. The results are shown in Table 2, which also presents results from MAGE-1, 2, 3 and 4 mRNA expression testing. There was no relationship observed between the 46 and 72 kDalton proteins.

TABLE II

DETECTION OF MAGE-1 PROTEIN AND THE 72-kDa PROTEIN IN CELL LINES BY WESTERN BLOTTING WITH MAbs 6Cl AND 6F12

| Cell lines | Western blot | | MAGE-mRNA expression |
|---|---|---|---|
| | MAGE-1 protein | 72-kDa protein | |
| [a]MZ2-MEL 3.1 | + | + | $1^\oplus, 2^\oplus, 3^\oplus, 4^\oplus$ |
| [a]MZ2-MEL 2.2 | − | + | $1^-, 2^\oplus, 3^\oplus, 4^-$ |
| [a]MZ2-MEL 2.2 ET1 | + | + | $1^\oplus, 2^\oplus, 3^\oplus, 4^-$ |
| [a]Mi13443 | + | + | $1^\oplus, 2^\oplus, 3^\oplus, 4^\oplus$ |
| [a]NA8-MEL | − | − | $1^-, 2^-, 3^-, 4^-$ |
| [a]IGR39 | − | − | $1^-, 2^-, 3^-, 4^-$ |
| [a]Me272.I.N2 | − | − | $1^-, 2^-, 3^\oplus, 4^-$ |
| [a]Me220 | − | − | $1^-, 2^-, 3^-, 4^-$ |
| [a]IGR3 | + | + | $1^\oplus, 2^\oplus, 3^\oplus, 4^\oplus$ |
| [a]Me204.A.1 | − | − | $1^-, 2^\oplus, 3^\oplus, 4^-$ |
| [a]Me242.B.1 | − | − | $1^-, 2^\oplus, 3^-, 4^-$ |
| [a]Me241.1 | + | + | $1^\oplus, 2^-, 3^\oplus, 4^-$ |
| [b]Me235 | + | + | $1^\oplus, 2^\oplus, 3^\oplus, 4^-$ |
| [a]Me192.2.20 | + | + | $1^\oplus, 2^\oplus, 3^\oplus, 4^\oplus$ |
| [a]Mi9 | − | − | $1^-, 2^\oplus, 3^\oplus, 4^-$ |
| [d]Mi13 | − | − | $1^-, 2^\oplus, 3^\oplus, 4$ |
| [a]Mi21 | − | − | $1^-, 2^-, 3^\oplus, 4^-$ |
| [a]Me248.3 | + | + | $1^\oplus, 2^\oplus, 3^\oplus, 4^\oplus$ |
| [a]Me244.1 | + | + | $1^\oplus, 2^\oplus, 3^-, 4^-$ |
| [a]Me222.6 | + | + | $1^\oplus, 2^\oplus, 3^\oplus, 4$ |
| [a]M14 | + | + | $1^\oplus, 2^\oplus, 3^\oplus, 4^\oplus$ |
| [b]Cl-18 | + | − | $1^\oplus, 2, 3^\oplus, 4^-$ |
| [b]U251 | − | − | $1^-, 2^-, 3^-, 4^-$ |
| [b]LN215 | + | + | $1^-, 2^\oplus, 3^\oplus, 4^-$ |
| [c]TF1 | − | − | $1^-, 2^-, 3^\oplus, 4^-$ |
| [c]HEL | + | − | $1^\oplus, 2^-, 3^-, 4^-$ |
| [d]MCF7 | − | − | $1^-, 2^-, 3^-, 4^-$ |
| [e]ACN | + | − | $1^\oplus, 2^\oplus, 3^\oplus, 4$ |
| [e]LAN-2 | + | + | $1^\oplus, 2^\oplus, 3^\oplus, 4^\oplus$ |
| [f]Fek4 | − | − | $1^-, 2^-, 3^-, 4^-$ |

[a]Melanoma; [b]glioblastoma; [c]myeloid leukemia; [d]breast carcinoma; [e]neuroblastoma; [f]fibroblast.

EXAMPLE 7

It is known that MAGE-1 expression can be induced, in vitro, in some MAGE-1 mRNA negative cell lines, by 5-aza-2'-deoxycytidine, a hypomethylating agent("DAC"). This agent was 5 incubated with three MAGE-1 mRNA negative cell lines (IGR 39, NA8-MEL, and U251), for 72 hours, after which lysates were taken, and incubated with monoclonal antibody 6C1. This treatment induced production of both the 46 kDa and the 72 kDa protein.

EXAMPLE 8

The intriguing results reported supra suggested further experiments to determine the identify of the 72 kDa protein. First, a melanoma expression library was prepared from melanoma cell line MZ2-M-L 43, using a commercially available system. Following the preparation, bacteriophages were plated (approximately $4 \times 10^5$ pfus), and transferred to nitrocellulose filters. These were then blocked with 5k milk powder in phosphate buffered saline, and then incubated with monoclonal antibody 6C1 (hybridoma supernatant diluted 1:4 in RPMI/10% fetal calf serum). The materials were then washed with PBS/0.5% Tween-20 and incubated with horseradish peroxidase conjugated sheep anti-mouse IgG, diluted 1:3000 in PBS/58 milk powder in PBS. Another wash, with 5% Tween-20 followed. Signals were detected using ECL, as discussed supra. All positive plaques were subjected to secondary and tertiary screening. Positives were then picked and transferred to a tube containing phage lysis buffer (20 mM Tris-HCl, pH 8.3, 50 mM KCl, 0.1% Tween 20), and an aliquot of this (5 ul) was used to amplify phage inserts. These were amplified via PCR, using:

GTGGCGACGA CTCCTGGAG (SEQ ID NO: 1)
and
CAGACCAACT GGTAATGGTA GCG (SEQ ID NO: 2)

which are λ primers. The cycling parameters were: 1 minute at 940° C., 1 minute at 610° C., and 1 minute at 720° C., for 30 cycles, followed by a final extension at 72° C., for 10 minutes.

A partial 5' sequence of the clones was then obtained, using a commercially available sequencing kit, using SEQ ID NO: 1. See Casanova, Meth. Mol. Biol. 23: 191–197 (1993). Twelve clones were sequenced, and three were found to be identical to that of the MAGE-10 cenomic sequence, as reported by DePlaen et al., Immunocenetics 40: 360–369 (1994), and Genbank Accession No. U10685.

One insert was then amplified, using SEQ ID NOS: 1 and 2, and a commercially available system. The cycling parameters for this amplification were 15 seconds at 940° C., 30 seconds at 610° C., 1 minute at 72° C. (10 cycles), 15 seconds at 940° C., 30 seconds at 610° C., 80 seconds plus 20 seconds cycle elongation at 72° C., for 20 cycles followed by 10 minutes at 720° C., for a final extension. The amplification product was cleaved with restriction endonucleases NotI and SalI, and then subcloned into Bluescript plasmid. Automated sequencing was then carried out using T3 and T7 primers. It was confirmed to be a partial MAGE-10 cDNA sequence (1400 base pairs), which corresponded to a start at position 2770 at the 5'-end, and extending 660 base pairs beyond the 3'-end of the genomic sequence reported by DePlaen, et al., supra.

EXAMPLE 9

Using the information obtained from the experiments described, supra, additional work was carried out to obtain a full length cDNA clone for MAGE-10.

As indicated, the partial cDNA clone was 1.4 kb long. This fragment was subjected to digestion with restriction endonucleases, and an HpaI fragment, corresponding to nucleotides 2770–3510 of the known, gDNA sequence, was isolated, and $^{32}p$ labeled, using a random priming DNA labeling kit. The labeled probe was then used to screen two libraries from a melanoma cell line (Lyse-4), in the vectors pcDNAI/Amp and pCEP4. The hybridization was carried out on filters, using 5×SSC, 5×Denhardt's, 0.5% SDS, and 100 ug/ml denatured salmon sperm DNA, at 65° C. Filters were then washed three times for 10 minutes at room temperature, with 1×SSC, 0.1% SDS, once for 20 minutes at 65° C., with 1×SSC, 0.1% SDS, and twice for 20 minutes at 65° C., with 0.1×SSC, 0.1% SDS. Ten positive clones were found, and sequenced automatically, using T7 and SP6 primers for the pcDNA I/Amp vector, and the pCEP-4 forward primer for pCEP-4. Several MAGE-10 clones were isolated, and fell into two categories (2.5 kb, and 1.5 kb, respectively), with different 3'-ends. The difference may result from alternate oligo (dT) priming during the cDNA synthesis for the library. The clones all seemed to be identical but for the first 50–70 nucleotides at the 5'-end. Comparison to the known, genomic sequence delineated existence of at least four exons, the last two being identical to those predicted by DePlaen, et al. supra (positions 1740–1814, and 1890-end). The second exon corresponded to positions 603–701, while the first exon did not appear to correspond to any previously recognized MAGE-10 sequence. The open reading frame was found in the last exon. A sequence is set forth at SEQ ID NO: 3. The first 100 bases or so indicate consensus sequences, based upon the collective sequence information secured via these experiments.

EXAMPLE 10

Three clones were isolated from the pcDNAI/Amp library, described supra, and were used for in vitro transcription and translation. These inserts were about 1.5 kilobases long, terminating at about position 3156, using genomic sequence enumeration. One ug of each DNA was translated, using a commercially available system, and a luciferase control plasmid was used as control. Translation products were subjected to PAGE analysis, and duplicate gels of non-radioactively labeled product were transferred to membranes, where Western Blotting was carried out, using mAb 6C1, or polyclonal antibodies prepared as described infra. Radiolabelled materials showed a 72 kilodalton protein from all three clones tested, suggesting that the mAb was cross reactive with MAGE-1 and MAGE-10.

EXAMPLE 11

Polyclonal antiserum against MAGE-10 was made as follows.

Immunogenic, MAGE-10 derived peptide (H)QDRIATTDDTTAMASASSSATGSFSYPE (OH)
(SEQ ID NO: 4), a portion of the deduced amino acid sequence of MAGE-10 was made, as were hybrids of this peptide and helper peptide P-30.

Helper Peptide P30 is well known, as per Valmori, et al., J. Immunol. 149: 717–721 (1992). It is a tetanus toxin T cell epitope, with amino acid sequence:

FNNFTVSFWLRVPKVSASHLE (SEQ ID NO: 5). Peptides were dissolved at 400 ug/ml in 100 mM Tris-HCl, pH 7.5, 0.9% NaCl. A rabbit was immunized over a 56 day period, with hybrid peptide (0.5 ml) at day 0, the MAGE-10 peptide (0.5 ml) at day 14, a second 0.5 ml injection of hybrid at day 28, and a final injection at day 56, of 0.5 ml of the MAGE-10 peptide. Antiserum produced in accordance with this protocol was tested for reactivity with MAGE-10 in various assays. Specifically, the in vitro translation product of expression of cDNA corresponding to SEQ ID NO: 3 was tested in Western blotting experiments, along the lines set forth supra. The antiserum was found to bind to a protein which was produced via the in vitro expression. It also recognized a 72 kDa band from melanoma lysates. In an ELISA, the polyclonal antibodies were found to recognize the MAGE-10 peptide.

The foregoing experiments describe the production of monoclonal antibodies which specifically bind to a tumor rejection antigen precursor TRAP.

The invention thus relates to MAGE-10 binding monoclonal antibodies and the hybridomas which produce them. The mAbs wee found to be useful in determining expression of MAGE-10. The mAbs can be added, e.g., in labeled form, bound to a solid phase, or otherwise treated to increase the sensitivity of MAGE-10 detection. Any of the standard types of immunoasays, including ELISAs, RIAs, competitive assays, agglutination assays, and all others are encompassed with respect to the way the mAbs can be used. The detection of MAGE-10 expression product is useful, e.g., in diagnosing or monitoring the presence or progression of a cancer.

The isolated, MAGE-10 protein is also a feature of this invention. This molecule has a molecular weight of about 72 kDa as determined by SDS-PAGE, and is useful as an immunogen as is the peptide of SEQ ID NO: 4, shown by the examples to be immunogenic. Preferably, these are used in combination with a suitable adjuvant.

Isolated cDNA encoding MAGE-10 is also a feature of this invention, such as the cDNA of SEQ ID NO: 3. Also a part of the invention are cDNA molecules which have complementary sequences that hybridize to SEQ ID NO: 3 under stringent conditions (e.g., 0.2×SSC, 0.1%k SDS at 65° C. or, more preferably, 0.1×SSC). These should include, as a minimum, nucleotides 164–574 of SEQ ID NO: 3, in 5' to 3' order. Nucleic acid molecules consisting of nucleotides 164–185, and 553–574 of SEQ ID NO: 3 are especially useful as probes and/or primers, and are also a part of this invention. The sequences can be used in the form of expression vectors when operably linked to promoters, and then used to transform or transfect cells, to produce various recombinant eukaryotic cell lines and prokaryotic cell strains. Similarly, the sequences, and sequences such as SEQ ID NOS: 1 and 2 can be used in various hybridization assays, such as PCR based assays. These are well known to the skilled artisan, and need not be repeated here.

The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. An immunogenic composition which comprises: (i) an isolated MAGE-10 tumor rejection antigen precursor which is encoded by a nucleic acid molecule which comprises, at a minimum, nucleotides 164–574 of SEQ ID NO: 3, and (ii) an adjuvant.

2. The immunogenic composition of claim 1, wherein said MAGE-10 tumor rejection antigen precursor has a molecular weight of about 72 Kilodaltons, as determined by SDS-PAGE.

3. The immunogenic composition of claim 1, wherein said isolated nucleic acid molecule comprises a nucleotide sequence, the complement of which hybridizes fully to nucleotides 67–2554 of SEQ ID NO: 3.

* * * * *